United States Patent [19]
Charlton

[11] Patent Number: 6,083,000
[45] Date of Patent: Jul. 4, 2000

[54] DENTAL HANDPIECE ATTACHMENT AND METHOD OF MAKING THE SAME

[76] Inventor: Daniel J. Charlton, 13983 Mango Dr., #101, Del Mar, Calif. 92104

[21] Appl. No.: 09/071,137

[22] Filed: Apr. 30, 1998

[51] Int. Cl.[7] .................................................. A61C 1/10
[52] U.S. Cl. ............................................. 433/82; 433/125
[58] Field of Search .................................. 433/82, 83, 125

[56] References Cited

U.S. PATENT DOCUMENTS

| | | | |
|---|---|---|---|
| 2,400,912 | 5/1946 | Britt et al. | 433/125 |
| 3,389,468 | 6/1968 | Lewis et al. | 433/82 |
| 4,315,741 | 2/1982 | Reichl | 433/125 |

Primary Examiner—John J. Wilson
Attorney, Agent, or Firm—Higgs, Fletcher & Mack LLP; Bernard L. Kleinke

[57] ABSTRACT

The dental handpiece attachment includes a housing defining a dental handpiece receiving portion and a central portion. A receiving opening in the receiving portion is in fluid communication with a cavity in the central portion to receive a drive mechanism responsive to a dental handpiece. A rotatable prophy cup assembly having a passageway therethrough is disposed at a prophy paste dispensing opening of the central portion cavity to enable a given amount of prophy paste sufficient for a single application, and stored within the housing, to be dispensed through the passageway and applied to the teeth. An actuator mechanism disposed within the receiving portion cooperates with a dental handpiece to urge the stored prophy paste out of the housing when the handpiece is received within the receiving portion.

12 Claims, 1 Drawing Sheet

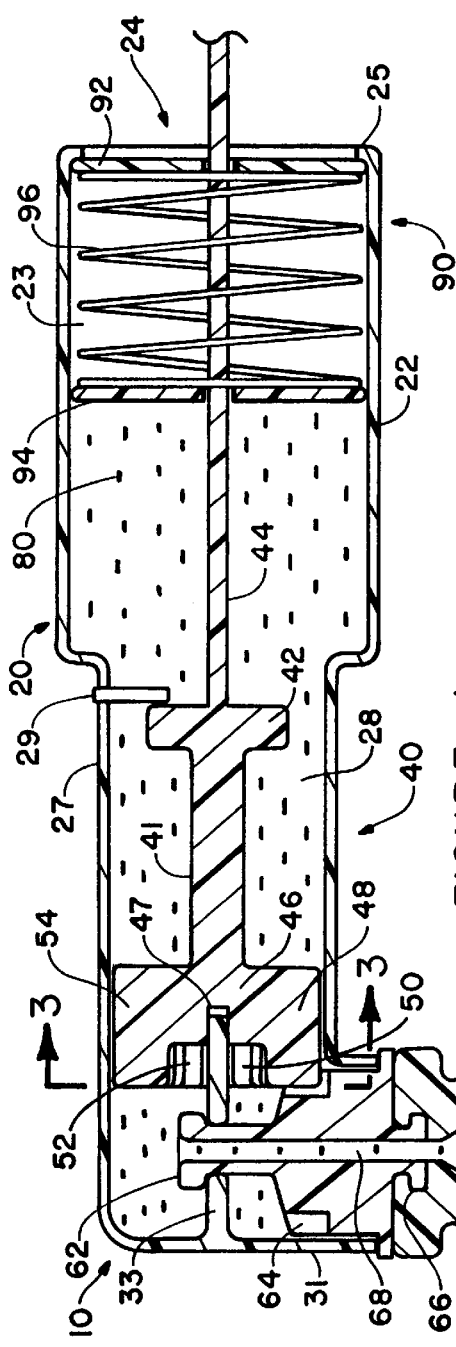
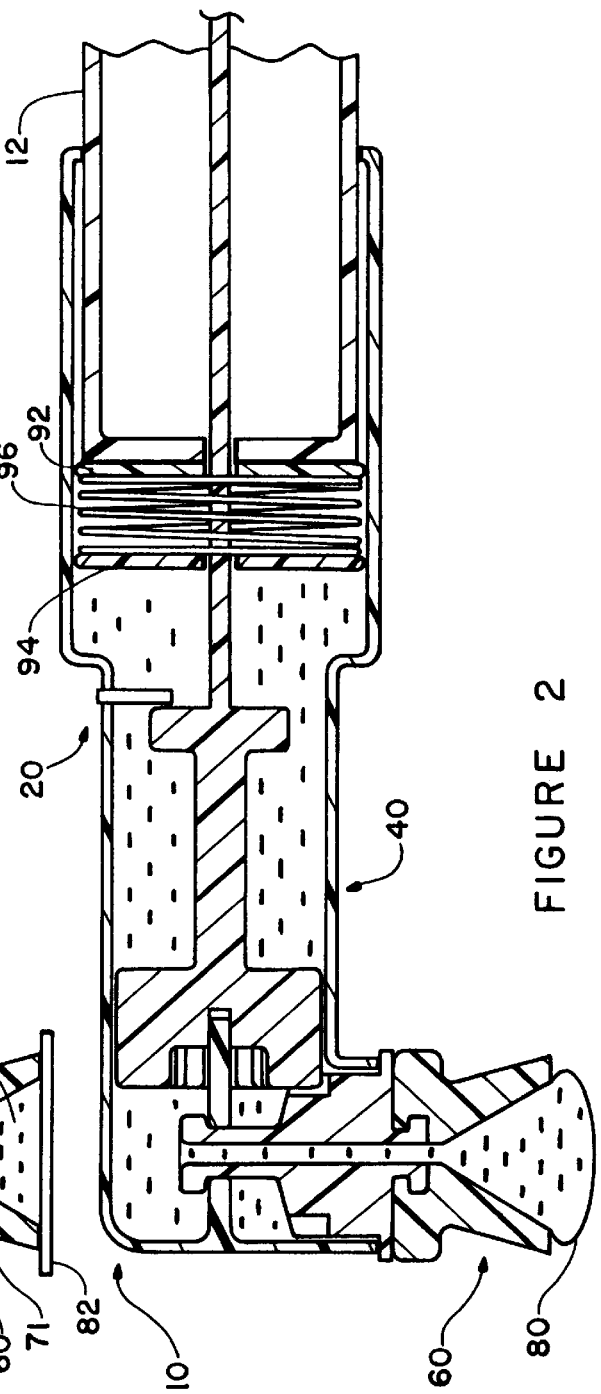
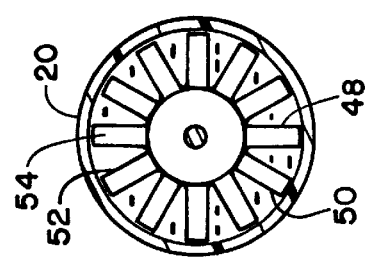
FIGURE 1
FIGURE 2
FIGURE 3

DENTAL HANDPIECE ATTACHMENT AND METHOD OF MAKING THE SAME

TECHNICAL FIELD

The present invention relates in general to a dental handpiece attachment and a method of making it. The invention more particularly relates to a dental handpiece attachment which may be used to dispense dental paste, such as prophy paste, and which can be made according to a novel method.

BACKGROUND ART

Typically, the cleaning of the teeth of a patient has been accomplished using a dental right angle attachment in cooperation with a standard dental hand piece. The right angle attachment included a prophy cup for applying prophy paste to the teeth. The dental hand piece was coupled to the dental right angle attachment to provide the prophy cup with rotary motion.

To apply the prophy paste to the teeth, a dental professional has been required to dip or insert the prophy cup into a container holding a supply of prophy paste therein. The prophy cup was then removed from the container along with a small amount of the prophy paste. By operating the dental handpiece, the prophy cup containing the small amount of prophy paste was rotated to enhance the cleaning process. Subsequently, the right angle was placed in the mouth of the patient and the prophy cup was urged against the teeth to apply the prophy paste thereto. This process was then repeated until the teeth were cleaned satisfactorily.

Such a tooth cleaning process has been unduly time consuming and inefficient as the application of the prophy paste was repeatedly interrupted by the need to reinsert the prophy cup into the container to obtain more prophy paste. Furthermore, the tooth cleaning apparatus and process has been awkward as two hands were required to clean the teeth of a patient. In this regard, one hand was needed to hold the prophy paste container, and another hand was required to hold the right angle attachment. Thus, either both hands of the dental professional were occupied to perform the cleaning operation, or the help of an assistant was required.

To enable the dental professional to apply prophy paste to the teeth of the patient in a non-awkward manner, various dental appliances have been introduced which combine a rotary dental prophylactic attachment with a dental paste dispenser. For example, reference may be made to U.S. Pat. Nos.: 2,300,828; 2,400,912; 2,728,528; 3,775,849; 3,977,084; and 5,062,716.

As disclosed in the aforementioned patents, reservoirs of dental prophy paste have been combined with dental prophylactic devices to enable the dental paste to be dispensed as the dental device is operated. In this manner, the dental professional is able to clean the teeth of the patient single handedly without interruption.

For example, U.S. Pat. No. 2,300,828 discloses a dental cleansing device having a hollow cylinder member coupled to a customary drill head. The cylinder member is sized to receive a suitable quantity of cleansing paste to clean the teeth of a patient. Similarly, U.S. Pat. No. 2,738,528 discloses a dental handpiece adapted to receive a container thereon for dispensing a cleansing paste.

While the disclosed devices could adequately dispense the cleansing paste, the cleansing paste storage containers were positioned on the outside of the dental device. The overall size of the device was increased, and maneuvering the device within the mouth of the patient was hampered as a result. Furthermore, the view of the dental professional was somewhat obstructed by the increased size.

Therefore, it would be highly desirable to have a new and improved dental device which facilitates the cleaning of teeth with one hand, and which substantially reduces any obstruction to the view of the dental professional operating the tool.

U.S. Pat. No. 3,977,084 discloses an electrically operated dental hygienic device. The device includes an internal reservoir of prophy paste and an electrically controlled dispensing mechanism to urge the prophy paste out into engagement with the teeth.

Although the disclosed device is self contained and somewhat reduced in size, the device is not adapted for use with standard dental tools, such as a dental handpiece. The use of the device unnecessarily duplicates some of the functions already provided by the standard dental tools used by the dental professional. Thus, the use of the disclosed device increases the cost to the dental professional to perform the tooth cleaning process.

Therefore, it would also be highly desirable to have a new and improved dental device which is adapted for use with standard dental tools.

U.S. Pat. Nos. 2,400,912; 3,775,849; and 5,062,796 disclose dental attachments adapted for use with standard dental equipment to clean teeth. The disclosed attachments include complex arrangements for storing a supply of paste within a sturdy housing. The devices utilize available compressed air or rotary motion provided by existing dental equipment to urge the stored paste out of the housing to apply to the teeth.

While the disclosed dental attachments have been capable of facilitating the cleaning of teeth, the devices have been relatively expensive to manufacture and purchase. Furthermore, the disclosed devices have required substantial cleaning operations after every use to ensure that sanitary conditions were maintained.

Therefore, it would be highly desirable to have a new and improved dental handpiece attachment for cleaning teeth that maintains sanitary conditions without requiring cleaning after each use, and which is relatively inexpensive to manufacture.

SUMMARY OF THE INVENTION

Therefore, the principal object of the present invention is to provide a new and improved dental handpiece attachment, and a method of making it, wherein the handpiece attachment dispenses prophy paste uninterruptively in a safe sanitary manner, and which is relatively inexpensive to manufacture.

Briefly, the above and further objects of the present invention are realized by providing a new and improved dental handpiece attachment that is sanitary, inexpensive to manufacture, and does not require cleaning after each use, and which can be made according to a novel method of the present invention.

The dental handpiece attachment includes a housing defining a dental handpiece receiving portion and a central portion. A receiving opening in the receiving portion is in fluid communication with a cavity in the central portion to receive a drive mechanism responsive to a dental handpiece. A rotatable prophy cup assembly having a passageway therethrough is disposed at a prophy paste dispensing opening of the central portion cavity to enable a given amount of prophy paste sufficient for a single application, and stored within the housing, to be dispensed through the passageway and applied to the teeth. An actuator mechanism disposed within the receiving portion cooperates with a dental handpiece to urge the stored prophy paste out of the housing when the handpiece is received within the receiving portion.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 1 is a longitudinal cross-sectional view of a dental handpiece attachment, which is constructed in accordance with the present invention;

FIG. 2 is a longitudinal cross-sectional view of the dental handpiece attachment of FIG. 1 illustrating the dispensing of stored prophy paste when a dental handpiece is received by the dental handpiece attachment; and FIG. 3 is a transverse cross-sectional view of the dental handpiece attachment of FIG. 1 taken along line 3—3 thereof.

BEST MODE FOR CARRYING OUT THE INVENTION

Referring now to the drawings, and more particularly to FIGS. 1 and 2 thereof, there is shown a dental handpiece attachment 10, which is constructed in accordance with the present invention. The attachment 10 is adapted for use with a standard dental handpiece 12 to quickly and easily clean the teeth of a patient, and can be made and used in accordance with the method of the present invention.

Preferably, the attachment 10 facilitates the cleaning of the teeth of a single patient. Upon completing the cleaning for the single patient, the attachment 10 can be disengaged from the dental handpiece 12 and disposed of in a sanitary manner. Thus, the attachment 10 is a single use device which does not require cleaning after each use.

The attachment 10 includes a housing or outer casing 20 defining a dental handpiece receiving portion 22 for receiving and engaging the hand piece 12. The housing further defines a central portion 27 having a cavity 28, and includes an annular wall 31 defining an aperture opening into the cavity 28 to enable the stored prophy paste 80 to exit the cavity 28.

An amount of prophy paste 80 is stored within the cavity 28 to aid in the cleaning of the teeth. The given amount corresponds to the particular patient. In this regard, an adult patient requires more prophy paste 80 than does a juvenile patient.

The prophy paste 80 is a standard prophy paste suitable for dental hygiene. However, to facilitate the flow of the prophy paste 80, the consistency of the prophy paste 80 may be adjusted. As will be described hereinafter in greater detail, the consistency may be adjusted according to the particular patient undergoing the tooth cleaning.

A tool mounting member 71 having a driven gear portion 64 and a passageway 68 extending completely through the member 71 is coupled rotatably at the dispensing opening to enable the stored prophy paste 80 to flow from the cavity 28 to the tool mounting member 71. Once at the tool mounting member 71, the flowing prophy paste 80 is applied to the teeth.

A drive assembly including a drive shaft 40 having a driving gear 46 is coupled to the driven gear portion 64 for rotating the tool mounting member 71. The drive assembly is enclosed within the housing 20 and substantially surrounded by the prophy paste 80. The consistency of the prophy paste 80, which enables it to flow, also enables the drive assembly to operate suitably for the single patient application of the prophy paste 80.

Disposed within the dental handpiece receiving portion 22, and in engagement with the stored prophy paste 80, is an actuator mechanism 90 for urging the stored prophy paste 80 out of the housing 20 automatically without manual intervention. The actuator mechanism 90 cooperates with the dental handpiece 12 to apply pressure on the stored prophy paste 80 only when the dental handpiece 12 is received within the dental handpiece receiving portion 22.

To maintain the stored prophy paste 80 in a sanitary condition, and to prevent the prophy paste 80 from becoming hard, a sanitary cover 82 is disposed over the passageway 68 to restrict the contact of ambient air with the prophy paste 80. The actuator mechanism 90 similarly provides a sanitary covering for the stored prophy paste 80. Alternatively, the entire attachment 10 can be packaged in a sealed envelope or bag (not shown) to maintain sanitary conditions.

In use, the dental handpiece attachment 10 (FIG. 2) is urged onto the dental handpiece 12, wherein the handpiece 12 is received within the handpiece receiving portion 22. The hand piece 12 engages the actuator mechanism 90, and urges it inwardly to initiate the dispensing of the stored prophy paste 80.

The dispensing of the prophy paste 80 is continued until such time that substantially all of the prophy paste 80 has been dispensed. Depending upon the given amount of stored prophy paste 80, its consistency, and the actuator mechanism 90, the cleaning time may range from about two minutes for a juvenile patient to about five minutes for an adult patient.

Upon the depletion of the stored prophy paste 80, the attachment 10 is removed from the handpiece 12 and discarded in an appropriate manner.

Considering now the housing 20 in greater detail with reference to FIGS. 1 and 2, the housing 20 is similar to the housings disclosed in U.S. Pat. Nos. 3,727,313 and 5,040,978, which Patent disclosures are incorporated by reference as if fully set forth herein. In this regard, the housing 20 is substantially L-shaped to define a right angle device.

The receiving portion 22 is substantially cylindrical and defines a cavity 23 for receiving the actuator mechanism 90. The receiving portion 22 includes an opening 24 for receiving the dental handpiece 12. An annular shoulder 25 cooperates with the actuator mechanism 90 to retain the actuator mechanism 90 within the receiving portion 22. The diameter of the receiving portion 22, the opening 24, and the shoulder 25 are sized and dimensioned to receive the standard dental handpiece 12. A detention member (not shown) selectively secures the receiving portion 22 to the handpiece 12.

The central portion 27 is also substantially cylindrical, and defines the cavity 28 to store the prophy paste 80 therein. The diameter of the central portion 27 is smaller than the diameter of the receiving portion to define a shoulder. The cavity 23 is disposed in fluid communication with the cavity 28 to facilitate dispensing the prophy paste 80.

As best seen in FIGS. 1 and 2, the prophy paste 80 is disposed substantially within the cavity 27. Preferably, an additional amount of prophy paste 80 is also stored within the cavity 23. The additional amount of prophy paste 80 within the cavity 23 permits the actuator mechanism 90 to engage the prophy paste 80 for urging it out of the housing 20. Alternatively, the length of the cavity 28 may be increased to accommodate additional prophy paste 80, and to accommodate the drift shaft 40.

The housing 20 further includes the annular wall 31 extending outwardly from the central portion 27 to define the dispensing opening. A retaining shelf 33 extending within the cavity 28 retains the tool mounting member 71 within the dispensing opening, and a retaining clip 29 extends through the central portion 27 to help secure the drive shaft assembly 40 within the housing 20.

Preferably, the housing 20 is constructed from a lightweight, inexpensive, material that is suitable for use under sanitary conditions. For example, a thermoplastic material would provide a suitable material.

Considering now the prophy paste 80 in greater detail, the given amount of prophy paste 80 is sufficient to meet the requirements of a particular patient. For example, a relatively small amount of prophy paste 80 may be stored in the cavity 28, and cavity 23, for young patients. A relatively large amount of prophy paste 80 will be stored for adult patients. In either case, the amount of prophy paste 80 stored in the housing 20 will be sufficient to complete a single application of the paste 80.

Thus, various attachments similar to attachment 10 can be manufactured and marketed which are specific to the age of the patient. For example, attachments for adult patients and attachments for young patients can be packaged, and identified, separately for use with an appropriate patient. In this way, the appropriate attachment may be selected by the dental professional for the patient.

The consistency of the stored prophy paste 80 will be selected to facilitate the flow of the paste 80, and to dispense the paste 80 at a rate suitable for the amount of paste 80 stored and the age of the patient. As described previously, the amount of the stored paste 80 is dependent upon the particular patient. To ensure that the dental professional is able to apply the given amount of prophy paste 80 to the teeth of the patient during an acceptable cleaning time period, the consistency of the prophy paste 80 may be adjusted.

In this regard, the consistency of the paste 80 can be substantially thick to increase the overall time during which the paste 80 will be dispensed without preventing the operation of the drive shaft assembly 40. On the other hand, the consistency of the stored paste 80 can be thinned to reduce the overall time for dispensing the prophy paste 80.

Preferably, the consistency of the prophy paste 80 will be selected to accommodate the patient according to the appropriate age group. For example, a typical cleaning operation for a juvenile patient is approximately two minutes. The cleaning operation for an adult patient is approximately five minutes. Therefore, the consistency of the prophy paste 80 is selected to enable the paste 80 to be dispensed for a cleaning time period of between about two minutes to about a period of about five minutes.

Or, where the attachments are produced specifically for certain age groups, a variety of attachments having paste of differing consistency may be provided. Thus, there may be attachments containing two minutes of paste and other attachments having five minutes of paste, or any other desirable consistency.

If desired, an excess amount of paste 80 may be stored to compensate for unintentionally wasted paste. Alternatively, a single amount of paste suitable for an adult, and including some excess paste, can be used for both adults and juveniles.

Considering now the tool mounting member 71 in greater detail, the tool mounting member 71 includes a lower flange portion 62 coupled rotatably within an opening in the shelf member 33, the driven gear portion 64, and an upper flange portion 66. The driven gear portion 64 includes a plurality of gear teeth (not shown) for cooperating with the driving gear portion 46 to rotate the tool mounting member 71.

The tool mounting member 71 further includes a prophy cup 73 having a convex opening in fluid communication with the passageway 68 is coupled to the upper flange 66 to apply the dispensed paste 80 to the teeth.

Considering now the drive shaft assembly 40 in greater detail with respect to FIGS. 1–3, the drive shaft assembly 40 includes an elongated shaft portion 44 which is received within the dental handpiece 12 (FIG. 2) to transfer power from the handpiece 12 to the attachment 10. The elongated shaft portion 44 is integrally connected to an enlarged shaft portion 42 which cooperates with the retaining clip 29 to retain the drive shaft assembly 40 within the housing 20.

The drive shaft assembly 40 further includes a central shaft portion 41 coupled integrally between the enlarged shaft portion 42 and the driving gear portion 46. A recess 47 in the driving gear portion 46 receives a projection from the shelf 33 to help stabilize the drive shaft assembly 40.

As best seen in FIG. 3, the driven gear portion 46 includes a central hub and a plurality of spaced apart gear teeth extending radially outwardly from the hub, including gear teeth 48, 50, 52 and 54. The gear teeth 48, 50, 52 and 54 extend to about the interior surface of the central portion 27 to define a bearing mechanism to further support the drive shaft assembly 40. To permit the stored prophy paste 80 to pass through the driven gear portion 46, the gear teeth 48, 50, 52 and 54 are spaced apart from one another. The spacing corresponds to the spacing between teeth on the driven gear portion 64 of the tool mounting member 71.

Considering now the actuator assembly 90 in greater detail, the assembly 90 includes a circular plate 92 for engaging the dental handpiece 12, a circular plate 94 for engaging the stored prophy paste 80, and a spring 96 coupled to the plates 92 and 94. The plates 92 and 94 are sized and dimensioned to correspond to the inner diameter of the receiving portion 22 to help prevent paste 80 from escaping around the periphery of the plate 92. The spring 96, if desired, may be secured to the plates 92 and 94.

The spring 96, in conjunction with the consistency of the paste 80, controls the rate at which the paste 80 is dispensed. Thus, by selecting a spring having a desired spring constant for use with a given paste consistency will enable the paste 80 to be delivered according to the preferred cleaning time periods. It will be understood by one skilled in the art that the paste consistencies and the spring constant can be selected without undue experimentation to achieve desirable results.

Although in the preferred embodiment the spring 96 is used, other resilient mechanisms may also be utilized to urge the paste 80 out of the housing 20 when compressed by the dental handpiece 12 received within the receiving portion 22.

A sanitary cover 82, secured to the prophy cup 71, cooperates with the plate 92, to restrict the contact between ambient air and the stored prophy paste 80 to substantially increase the shelf life of the prophy paste.

While particular embodiments of the present invention have been disclosed, it is to be understood that various different modifications are possible and are contemplated within the true spirit and scope of the appended claims.

There is no intention, therefore, of limitations to the exact abstract or disclosure herein presented.

What is claimed is:

1. A dental handpiece attachment for use with a dental handpiece, comprising:

housing means for engaging the handpiece, said housing means defining a handpiece receiving portion having a receiving opening to receive the handpiece therein, and a central portion having a cavity in fluid communication with said receiving opening and a prophy paste dispensing aperture opening to said cavity;

a given amount of prophy paste sufficient for a single patient application stored within said cavity;

prophy cup means disposed rotatable at said dispensing aperture and having a passageway extending into said cavity for dispensing said stored prophy paste, said passageway terminating within said cavity to enable said stored prophy paste to flow out of said cavity through said passageway;

drive means disposed within said housing, substantially surrounded by said stored prophy paste, and coupled to said prophy cup means for rotating said prophy cup means;

actuator means disposed within said receiving portion, and responsive to the handpiece being received within the receiving portion, for urging said stored prophy paste out of said cavity through said passageway to facilitate dispensing said stored prophy paste with said prophy cup means for said single patient application; and wherein said actuator means includes a place member for engaging said stored prophy paste and a resilient member for urging said plate member away from a received handpiece at a substantially constant rate to enable said stored prophy paste to be dispensed in a controlled manner.

2. A dental handpiece attachment according to claim 1, wherein said prophy paste has a given consistency to enable said prophy paste urged at said constant rate to be dispensed for a cleaning time preferably between about two minutes and about five minutes.

3. A dental handpiece attachment according to claim 2, wherein said cleaning time is more preferably about two minutes.

4. A dental handpiece attachment according to claim 2, wherein said cleaning time is more preferably about five minutes.

5. A dental handpiece attachment according to claim 1, wherein said housing is constructed from a thermoplastic material.

6. A dental handpiece attachment according to claim 1, wherein said drive means includes bearing means having gaps therethrough to enable said stored prophy paste to pass through said bearing means when said actuator means urges said stored prophy paste.

7. A dental handpiece attachment according to claim 1, wherein said resilient member includes a spring.

8. A dental handpiece attachment according to claim 1, further including a cover disposed over said passage for restricting the contact of ambient air with said stored prophy paste.

9. A method of making a dental handpiece attachment for use with a dental handpiece, comprising:

constructing a housing including a handpiece receiving portion having a receiving opening to receive the handpiece therein, and a central portion having a cavity in fluid communication with said receiving opening and a prophy paste dispensing aperture opening to said cavity;

introducing a given amount of prophy paste sufficient for a single patient application into said cavity;

disposing rotatably a prophy cup means having a passageway at said dispensing aperture for dispensing said prophy paste, and said passageway terminating within said cavity to enable said prophy paste to flow out of said cavity through said passageway;

disposing a drive means within said housing substantially surrounded by said prophy paste;

coupling said drive means to said prophy cup means for rotating said prophy cup means;

disposing an actuator means, responsive to the handpiece being received within the receiving portion, within said receiving portion; and further including engaging stored prophy paste with a plate member, and coupling a resilient member to said plate member for urging said plate member away from a received handpiece at a substantially constant rate to enable said stored prophy paste to be dispensed in a controlled manner.

10. A method according to claim 9, further including preparing said prophy paste to have a given consistency to enable said prophy paste to be dispensed for a cleaning time preferably between about two minutes and about five minutes.

11. A method according to claim 9, further including constructing said housing out of a thermoplastic material.

12. A method according to claim 9, further including disposing a protective covering over said prophy cup means to restrict the contact of ambient air with said stored prophy pastes.

* * * * *